(12) United States Patent
Chen et al.

(10) Patent No.: US 8,148,549 B2
(45) Date of Patent: Apr. 3, 2012

(54) PREPARATION OF (S)-(+)-N-METHYL-3-(1-NAPHTHYLOXY)-3-(2-THIENYL) PROPYLAMINE USING OPTICALLY ACTIVE METHYLHYDROXYLAMINOPROPANOL COMPOUND AS AN INTERMEDIATE

(75) Inventors: Bo-Fong Chen, Taoyuan (TW); Jinun-Ban Yeh, Taoyuan (TW); Wei-Chyun Wong, Taoyuan (TW)

(73) Assignee: SCI Pharmtech, Inc. (TW)

( * ) Notice: Subject to any disclaimer, the term of this patent is extended or adjusted under 35 U.S.C. 154(b) by 420 days.

(21) Appl. No.: 12/402,740

(22) Filed: Mar. 12, 2009

(65) Prior Publication Data

US 2010/0234619 A1    Sep. 16, 2010

(51) Int. Cl.
*C07D 333/12* (2006.01)
*C07D 333/20* (2006.01)

(52) U.S. Cl. .......................................................... 549/75
(58) Field of Classification Search ...................... 549/75
See application file for complete search history.

(56) References Cited

U.S. PATENT DOCUMENTS 5,023,269 A * 6/1991 Robertson et al. ............. 514/438
7,829,731 B2 * 11/2010 Chen et al. ....................... 549/75

* cited by examiner

*Primary Examiner* — Susannah Chung
(74) *Attorney, Agent, or Firm* — Berliner & Associates

(57) ABSTRACT

The present invention provides a (S)-methylhydroxylaminopropanol derivative as an intermediate for preparation of (S)-(+)-N-methyl-3-methyl-3-(1-naphthyloxy)-3-(2-thienyl) propylamine. The present invention also provides a process for preparing (S)-(+)-N-methyl-3-methyl-3-(1-naphthyloxy)-3-(2-thienyl)propylamine with higher yield and lower cost, wherein the (S)-methylhydroxylaminopropanol derivative is used as an intermediate.

15 Claims, No Drawings

PREPARATION OF (S)-(+)-N-METHYL-3-(1-NAPHTHYLOXY)-3-(2-THIENYL)PROPYLAMINE USING OPTICALLY ACTIVE METHYLHYDROXYLAMINOPROPANOL COMPOUND AS AN INTERMEDIATE

BACKGROUND OF THE INVENTION

1. Field of the Invention

The present invention relates to a novel preparation of (S)-(+)-N-methyl-3-(1-naphthyloxy)-3-(2-thienyl)propylamine, by using chiral methylhydroxylaminopropanol derivative as an intermediate.

2. Description of Related Art (S)-(+)-N-methyl-3-(1-naphthyloxy)-3-(2-thienyl)propylamine (Duloxetine®) is an antidepressant drug developed by Eli Lilly and Company, Inc. Various methods have been reported to prepare Duloxetine®. For example, U.S. Pat. No. 5,023,269 discloses a process as shown in the following scheme:

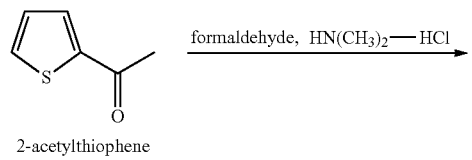
2-acetylthiophene

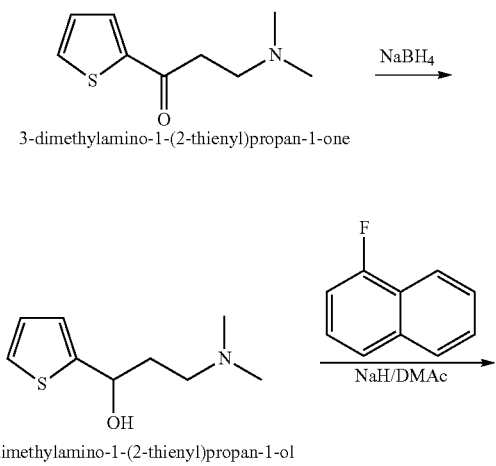
3-dimethylamino-1-(2-thienyl)propan-1-one 3-dimethylamino-1-(2-thienyl)propan-1-ol

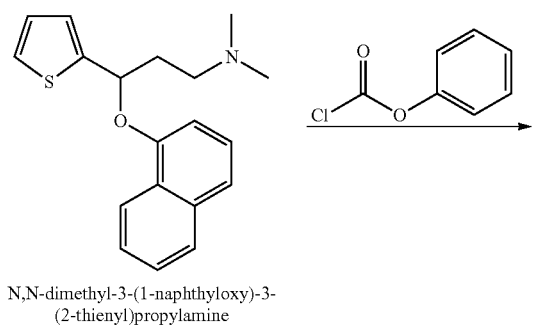
N,N-dimethyl-3-(1-naphthyloxy)-3-(2-thienyl)propylamine

-continued

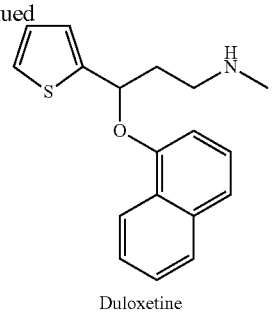
Duloxetine

In this example, 2-acetylthiophene is used as the starting material for reacting with formaldehyde and dimethylamine to form a Mannich product namely 3-dimethylamino-1-(2-thienyl)propan-1-one. A hydride reduction is performed on this propanone to form corresponding 3-dimethylamino-1-(2-thienyl)propan-1-ol. The resulting propanol is then reacted with fluoronaphthalene to form N,N-dimethyl-3-(1-naphthyloxy)-3-(2-thienyl)propylamine. Subsequently, racemic Duloxetine® is obtained by demethylation of this propylamine. In this process, the yield of demethylation is very low, about 41%. In addition, Duloxetine® produced via this route is racemic. Resolution is therefore needed to obtain chiral Duloxetine which renders this process less competitive.

SUMMARY OF THE INVENTION

In light of the above-mentioned drawbacks of the prior art, the present invention provides a novel (S)-methylhydroxylaminopropanol derivative of formula (II)

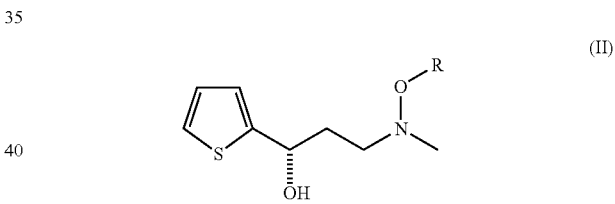
(II)

wherein R is a hydrogen atom, an alkyl group having 1 to 8 carbon atoms or an aryl group having 6 to 10 carbon atoms. Furthermore, the absolute configuration of the chiral center is S.

In the present invention, the (S)-methylhydroxylaminopropanol of formula (II) is used as an intermediate for preparing (S)-(+)-N-methyl-3-(1-naphthyloxy)-3-(2-thienyl)propylamine (Duloxetine®).

The present invention provides a process for preparing (S)-(+)-N-methyl-3-(1-naphthyloxy)-3-(2-thienyl)propylamine (Duloxetine®) with higher yield and lower cost by using the (S)-methylhydroxylaminopropanol derivative of formula (II) as the intermediate, and therefore higher yield can be obtained at lower cost.

In the present invention, the process for preparing Duloxetine of the present invention includes steps of: (i) performing a Mannich reaction of 2-acetylthiophene, formaldehyde and a methylhydroxylamine of formula, $HNCH_3(OR)$, to form a substituted amino ketone of formula (I); (ii) reducing the substituted amino ketone of formula (I) enatio selectively to form a (S)-methylhydroxylaminopropanol derivative of formula (II); (iii) performing reaction of this (S)-methylhydroxylaminopropanol (II) with halonaphthalene to form N-methyl-N-hydroxyl-3-(1-naphthyloxy)-3-(2-thienyl)propylamine derivative (III); and (iv) performing an N,O-cleavage reaction of the propylamine derivative (III) to form Duloxetine;

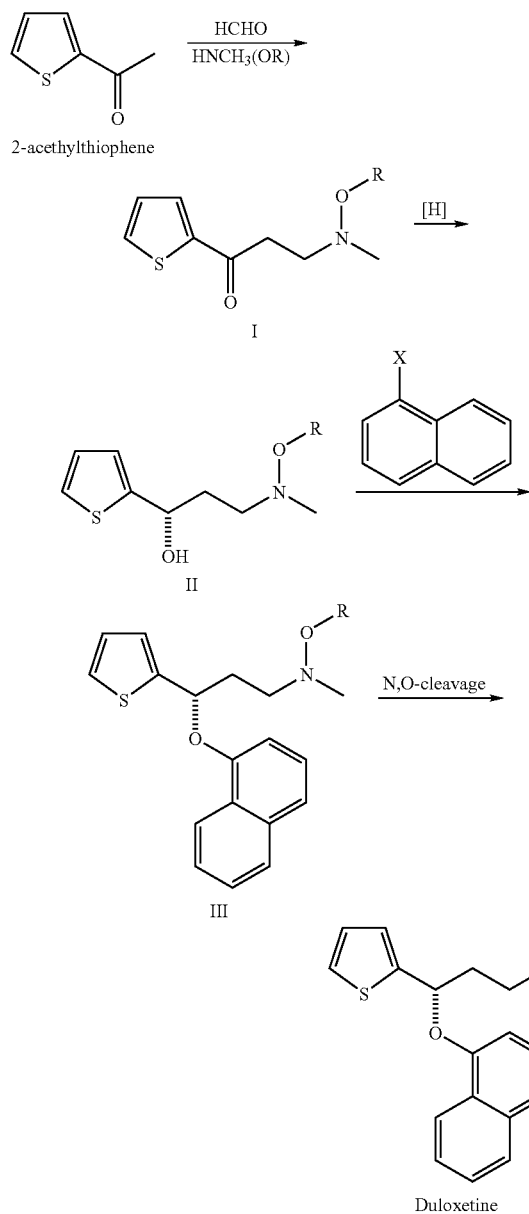

wherein R is a hydrogen atom, an alkyl group having 1 to 8 carbon atoms or an aryl group having 6 to 10 carbon atoms.

DETAILED DESCRIPTION OF PREFERRED EMBODIMENTS

The following illustrative embodiments are provided to illustrate the disclosure of the present invention, these and other advantages and effects can be apparently understood by those in the art after reading the disclosure of this specification. The present invention can also be performed or applied by other different embodiments. The details of the specification may be on the basis of different points and applications, and numerous modifications and variations can be devised without departing from the spirit of the present invention.

The present invention provides a novel methylhydroxylaminopropanol derivative of formula (II) in optical active form:

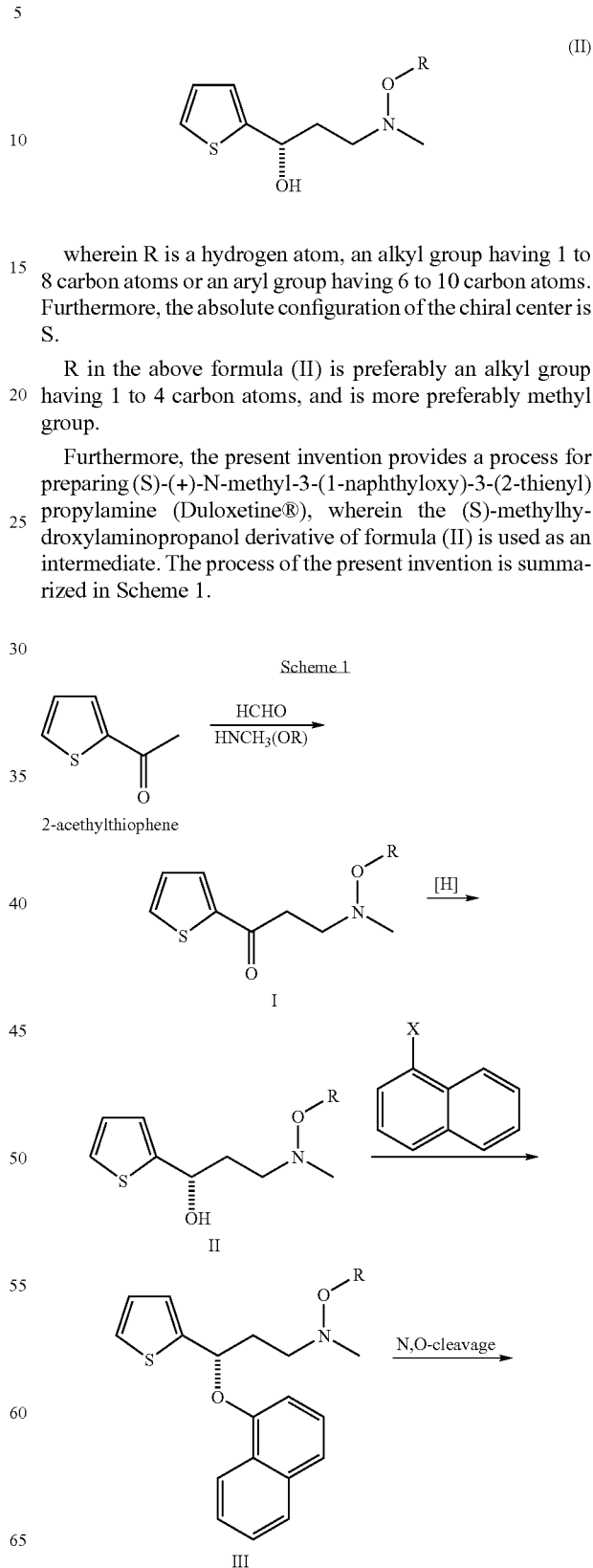

wherein R is a hydrogen atom, an alkyl group having 1 to 8 carbon atoms or an aryl group having 6 to 10 carbon atoms. Furthermore, the absolute configuration of the chiral center is S.

R in the above formula (II) is preferably an alkyl group having 1 to 4 carbon atoms, and is more preferably methyl group.

Furthermore, the present invention provides a process for preparing (S)-(+)-N-methyl-3-(1-naphthyloxy)-3-(2-thienyl) propylamine (Duloxetine®), wherein the (S)-methylhydroxylaminopropanol derivative of formula (II) is used as an intermediate. The process of the present invention is summarized in Scheme 1.

-continued

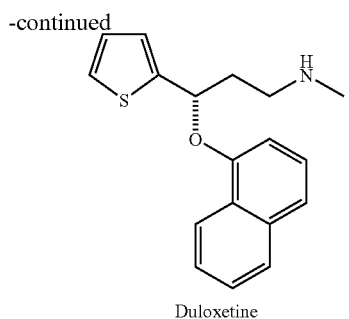
Duloxetine

In Scheme 1, R is a hydrogen atom, an alkyl group having 1 to 8 carbon atoms or an aryl group having 6 to 10 carbon atoms.

In more details, the process of the present invention includes steps of:
(i) performing a Mannich reaction of 2-acetylthiophene, formaldehyde and a methylhydroxylamine of formula, HNCH$_3$(OR), to form a substituted amino ketone of formula (I);
(ii) reducing the substituted amino ketone of formula (I) enatio selectively to a (S)-methylhydroxylaminopropanol derivative of formula (II);
(iii) producing N-methyl-N-hydroxyl-3-(1-naphthyloxy)-3-(2-thienyl)propylamine derivative (III) by reacting (S)-methylhydroxylaminopropanol (II) with halonaphthalene; and
(iv) performing an N,O-cleavage reaction of the propylamine derivative (III) to form Duloxetine.

The step (i) of the process is carried out at a temperature ranged from 90° C. to 15° C., preferably 80° C. to 40° C., and more preferably 70° C. to 50° C. The substituted amino ketone of formula (I) obtained in the step (i) is either as a free form or as an acid addition salt.

The reduction of the substituted amino ketone of formula (I) in the step (ii) is performed by asymmetric reduction, and the resulting optically active form of the (S)-methylhydroxylaminopropanol derivative of formula (II) is obtained. The optically active form can be obtained via asymmetric hydrogenation using catalyst with chiral ligands or hydride with chiral ligands.

In one preferred embodiment, reduction of the substituted amino ketone of formula (I) in the step (ii) is carried out in a mixture of an alcohol such as methanol and base such as potassium tert-butoxide, in the presence of catalyst that comprising an enantiomer-enriched bidentate phosphorus-containing ligand, a transition metal and a diamine, preferably a chiral diamine, such as RuCl$_2$((R)-3,5-xylylBINAP) ((2R)-DAIPEN). The reaction mixture is hydrogenated at predetermined pressure to yield (S)-methylhydroxylaminopropanol with high ee value.

The reaction of (S)-methylhydroxylaminopropanol (II) with halonaphthalene to form N-methyl-N-hydroxyl-3-(1-naphthyloxy)-3-(2-thienyl)propylamine derivative (III) in the step (iii) is carried out by using appropriate base in a suitable aprotic solvent.

In one preferred embodiment, (S)-methylhydroxylaminopropanol (II) is reacted with fluoronaphthalene in DMF using sodium hydride as base. The reaction is carried out at a temperature ranged from 110° C. to 10° C., preferably 70° C. to 40° C., for 1 to 24 hours.

The N,O-cleavage reaction of the propylamine derivative (III) in the step (iv) of the process is carried out by hydrogenation in the presence of a catalyst such as Raney-nickel, or by chemical reduction methods such as those using LiAlH$_4$ or zinc metal as reducing agent.

In one preferred embodiment, the propylamine derivative (III) is hydrogenated in methanol in the presence of Raney-nickel at a temperature ranged from 80° C. to 15° C., preferably 70° C. to 40° C., for 9 to 15 hours.

Compared with the conventional process, Duloxetine can be obtained optically pure with higher yield and lower cost from the process of the present invention. This process should operate particularly well on an industrial scale having regard to economic and ecological aspects.

EXAMPLES

Example 1

Synthesis of 3-methoxymethylamino-1-(2-thienyl)-1-propanone hydrochloride salt

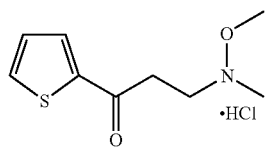

27.7 g of N,O-dimethylhydroxylamine hydrochloride, 9.3 g of paraformaldehyde, 6.4 g of 32% hydrochloride, 30.0 g of 2-acetylthiophene and 100 g of isopropanol were provided into a flask. After being stirred at 60° C. for 13 hours, the reaction mixture was cool down to room temperature. The crystal thus formed was filtered, washed with 30 g of isopropanol and dried under reduced pressure, and then 42.5 g of 3-methoxymethylamino-1-(2-thienyl)-1-propanone hydrochloride salt (75.9%) is obtained. $^1$H NMR (400 MHz, CDCl$_3$) δ (ppm)=3.1 (s,3H), 3.7-3.8 (br, 4H), 4.1 (s,3H), 7.2 (t, J=4.5 Hz, 1H), 7.7 (d, J=4.9 Hz, 1H), 7.9 (d, J=3.5 Hz, 1H).

Example 2

Synthesis of (S)-3-methoxymethylamino-1-(2-thienyl)propan-1-ol

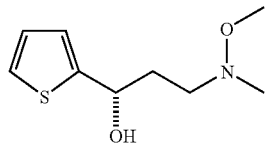

4 mL of degassed methanol solution containing 10 mg of RuCl$_2$((R)-3,5-xylylBINAP) ((2R)-DAIPEN), 160 mg of 3-methoxymethylamino-1-(2-thienyl)-1-propanone, 100 mg of potassium tert-butoxide and 10 mL of methanol were charged in a glass autoclave under an argon gas flow. After deaeration and replacement by argon, hydrogen was introduced to a predetermined pressure. The resulting solution was hydrogenated at 20□ for 12 hours. Upon completion of hydrogenation the reaction mixture was concentrated, and then the desired compound is obtained as an oily product (161 mg, 95.8% by HPLC assay, 95% ee). $^1$H NMR (400 MHz, CDCl₃) δ (ppm) 3.0 (s, 3H), 3.0-3.1 (m, 1H), 4.1 (s, 3H), 4.0-4.1 (m, 3H), 6.1 (dt, J=7.4, 15.4 Hz, 1H), 6.9 (d, J=15.7 Hz, 1H), 7.0 (dd, J=3.7, 5.0 Hz, 1H), 7.1 (d, J=3.4 Hz, 1H).

Example 3

Synthesis of N-methyl-N-methoxyl-3-(1-naphthyloxy)-3-(2-thienyl)propylamine

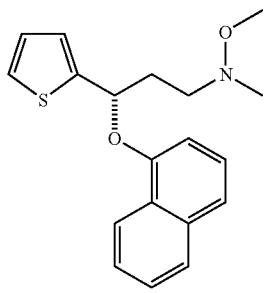

10.0 g of (S)-3-methoxymethylamino-1-(2-thienyl)propan-1-ol from example 2 was dissolved in 30 mL of N,N-dimethylformamide at ambient temperature, to which was added sodium hydride (3.9 g, 60%) with vigorous stirring. Then, 9.4 g of 1-fluoronaphthalene was added and the mixture was stirred at 70° C. for 8 hours. Upon completion of naphthalenation, the reaction mixture was quenched with water (90 mL). After extraction with toluene (30 mL×3), the organic layer was combined and concentrated. Subsequently, the crude product was purified by silica gel column chromatography to give objective compound as an amber oil (13.5 g, 82.8%). ¹H NMR (400 MHz, CDCl₃) δ (ppm)=2.3 (m, 1H), 2.5 (m, 1H), 2.6 (s, 3H), 2.9 (t, 2H), 3.5 (s, 3H), 5.8 (m, 1H), 6.8 (m, 1H), 6.9 (d, 1H), 7.0 (s, 1H), 7.2 (d, 1H), 7.3 (m, 1H), 7.4 (d, 1H) 7.5 (m, 2H), 7.8 (d, 1H), 8.3 (d, 1H).

Example 4

Synthesis of (S)-(+)-N-methyl-3-methyl-3-(1-naphthyloxy)-3-(2-thienyl)propylamine (Duloxetine)

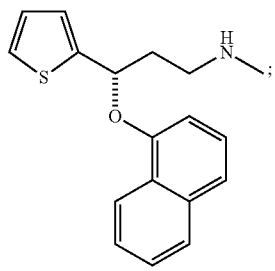

N-methyl-N-methoxyl-3-(1-naphthyloxy)-3-(2-thienyl) propylamine obtained in example 3 was dissolved in 15 mL of methanol with 0.67 g of Raney-nickel were charged in a glass autoclave. The resulting solution was hydrogenated at 50□ for 12 hours. Upon completion of hydrogenation the reaction mixture was filtered and solvent is removed under reduced pressure, and then the desired compound is obtained as an oily compound (12.0 g, 96.4% by HPLC assay). ¹H NMR (400 MHz, CDCl₃) δ (ppm)=2.2 (m, 1H), 2.4 (m, 1H), 2.4 (s, 3H), 2.8 (m, 2H), 5.8 (m, 1H), 6.8 (d, 1H), 6.9 (m, 1H), 7.1 (d, 1H), 7.2 (d, 1H), 7.3 (d, 1H), 7.4 (m, 1H), 7.5 (m, 2H), 7.8 (m, 1H), 8.3 (m, 1H).

The foregoing descriptions of the detailed embodiments are only illustrated to disclose the features and functions of the present invention and not restrictive of the scope of the present invention. It should be understood to those in the art that all modifications and variations according to the spirit and principle in the disclosure of the present invention should fall within the scope of the appended claims.

What is claimed is:
1. A process for preparing (+)-(S)-N-methyl-3-(1-naphthyloxy)-3-(2-thienyl) propylamine, comprising steps of:
(i) performing a Mannich reaction of 2-acetylthiophene, formaldehyde and a methylhydroxylamine of formula, HNCH₃(OR), to form a substituted amino ketone of formula (I)

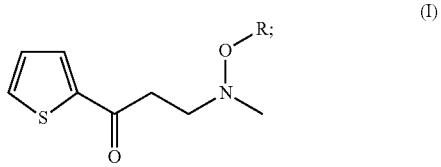

(ii) reducing the substituted amino ketone of formula (I) enatio selectively to a (S)-methylhydroxylaminopropanol compound of formula (II)

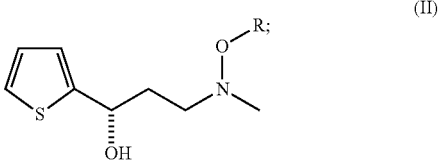

(iii) performing a reaction of the (S)-methylhydroxylaminopropanol compound of formula (II) with halonaphthalene to form N-methyl-N-hydroxyl-3-(1-naphthyloxy)-3-(2-thienyl)propylamine compound

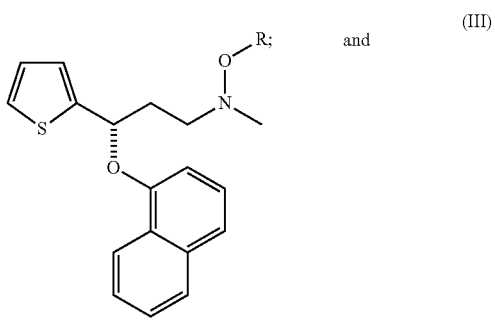

(iv) performing an N, O-cleavage reaction of the N-methyl-N-hydroxyl-3-(1-naphthyloxy)-3-(2-thienyl)propylamine compound (III) to form (+)-(S)-N-methyl-3-(1-naphthyloxy)-3-(2-thienyl) propylamine,
wherein R is a hydrogen atom, an alkyl group having 1 to 8 carbon atoms or an aryl group having 6 to 10 carbon atoms.

2. The process according to claim 1, wherein the substituted amino ketone of formula (I) obtained in the step (i) is a free form or an acid addition salt.

3. The process according to claim 1, wherein the step (ii) is performed by chiral reduction.

4. The process according to claim 3, wherein the (S)-methylhydroxylaminopropanol compound of formula (II) is in an optically active form.

5. The process according to claim 3, wherein the chiral reducing agent used in the chiral reduction is selected from the group consisting of complex hydride, borane, transition metal catalyst and microbial dehydrogenase.

6. The process according to claim 5, wherein a reduction catalyst comprising an enantiomer-enriched bidentate phosphorus-containing ligand, a transition metal and a diamine is used.

7. The process according to claim 6, wherein the diamine is a chiral diamine.

8. The process according to claim 1, wherein the reaction in the step (iii) is carried out by using appropriate base in suitable aprotic solvent at a temperature ranged from 110° C. to 10° C.

9. The process according to claim 1, wherein the N,O-cleavage reaction of the N-methyl-N-hydroxyl-3-(1-naphthyloxy)-3-(2-thienyl)propylamine compound (III) in the step (iv) is carried out by hydrogenation in an alcohol in the presence of Raney-nickel at a temperature ranged from 80° C. to 15° C.

10. The process according to claim 1, wherein the N,O-cleavage reaction of the N-methyl-N-hydroxyl-3-(1-naphthyloxy)-3-(2-thienyl)propylamine compound (III) in the step (iv) is carried out by a chemical reduction using $LiAlH_4$ or zinc metal as a reducing agent.

11. The process according to claim 1, wherein the step (i) is performed at a temperature ranged from 90° C. to 15° C.

12. The process according to claim 1, wherein the step (ii) is performed at a pH value ranged from 6 to 14.

13. A process for preparing the (S)-methylhydroxylaminopropanol compound of formula (II) according to claim 1, comprising steps of:
(i) performing a Mannich reaction of 2-acetylthiophene, formaldehyde and a methylhydroxylamine of formula, $HNCH_3(OR)$, to form a substituted amino ketone of formula (I); and
(ii) reducing the substituted amino ketone of formula (I) enatio selectively to a (S)-methylhydroxylaminopropanol compound of formula (II).

14. The process according to claim 13, wherein the step (i) is performed at a temperature ranged from 90° C. to 15° C.

15. The process according to claim 13, wherein the step (ii) is performed at pH value ranged from 6 to 14.

* * * * *